United States Patent [19]

Jörnéus et al.

[11] Patent Number: 5,269,685
[45] Date of Patent: Dec. 14, 1993

[54] ANCHORING MEMBER

[75] Inventors: Lars Jörnéus, Frillesas; Anders Boss, Mölndal, both of Sweden

[73] Assignee: Nobelpharma AB, Gothenburg, Sweden

[21] Appl. No.: 935,993

[22] Filed: Aug. 27, 1992

[30] Foreign Application Priority Data

Aug. 27, 1991 [SE] Sweden ............................ 9102451

[51] Int. Cl.5 ............................................. A61C 8/00
[52] U.S. Cl. ..................................... 433/174; 433/173
[58] Field of Search .............. 433/173, 174, 175, 176; 411/386, 387, 418, 420, 421

[56] References Cited

U.S. PATENT DOCUMENTS

| | | | |
|---|---|---|---|
| 4,407,620 | 10/1983 | Shinjo | 411/387 |
| 4,468,200 | 8/1984 | Munch | 433/174 |
| 4,713,004 | 12/1987 | Linkow et al. | 433/174 |
| 4,730,969 | 3/1988 | Dohi | 411/387 |
| 4,781,506 | 11/1988 | Roberts et al. | 411/387 |
| 5,064,425 | 11/1991 | Branemark et al. | 433/174 X |

FOREIGN PATENT DOCUMENTS

| | | |
|---|---|---|
| 0237505 | 9/1987 | European Pat. Off. . |
| 0323559 | 7/1989 | European Pat. Off. . |
| 0458258 | 11/1991 | European Pat. Off. . |
| 3626172 | 2/1988 | Fed. Rep. of Germany ...... 411/386 |
| 9002823 | 5/1990 | Fed. Rep. of Germany . |

Primary Examiner—Gene Mancene
Assistant Examiner—Nicholas D. Lucchesi
Attorney, Agent, or Firm—Pollock, Vande Sande & Priddy

[57] ABSTRACT

A screw-shaped titanium anchoring member for permanent anchorage in bone tissue, specifically permanent anchorage of artificial teeth or tooth bridges in the jaw-bone, comprises at least one cavity located at the forward tip of the screw, the edges of the at least one cavity on the outer threaded cylindrical surface forming cutting tooth with cutting edge to provide self-tapping when the anchoring member is screwed into a bored hole in the bone tissue and the total volume of the at least one cavity being adapted to contain the scraped-off bone tissue material. The anchoring member on the outer cylindrical surface of the cutting tooth, a short distance behind its cutting edge, is provided with a clearance surface defined on the outer surface of the anchoring member, which when seen in a cross-section through the cutting part of the anchoring member, is slightly bevelled a short distance behind the threaded cutting edge.

6 Claims, 1 Drawing Sheet

ANCHORING MEMBER

FIELD OF THE INVENTION

The present invention relates to a screw-shaped anchoring member made of titanium for permanent anchorage in bone tissue, specifically permanent anchorage of artificial teeth and tooth bridges in the jaw bone. The tip of the anchoring member comprises at least one cavity. The edges of the cavities on the outer cylindrical surface form cutting edges to provide self-tapping when the anchoring member is screwed into the bone tissue. The total volume of the cavities is adapted to contain the scraped-off bone tissue material, that is the bone tissue material is contained within the volume formed by the cavities.

BACKGROUND OF THE INVENTION

An anchoring member of this type, a so-called fixture, is previously known by EP 0 237 505. In this case the cavities are formed from two perpendicular through holes which are perpendicular to the longitudinal axis of the fixture or by three not through-going cavities formed on the outer, circular surface of the anchoring member so that cutting edges having a positive cutting angle are formed.

The advantage of a self-tapping fixture is the fact that the fixture can be more easily installed in the jaw-bone. In the normal procedure for installing a fixture a hole is drilled in the jaw-bone. Then drills with successively increasing drilling diameters are used until the hole diameter corresponds to the root diameter of the threaded fixture. In the normal surgical method indicated by Dr Brånemark a screw tap is used to form the internal thread into which the threaded part of the fixture is inserted. When using a self-tapping fixture of the above-mentioned type the installation can be carried out without any screw tap.

The hardness of the bone (jaw-bone) into which the fixtures are installed varies to a big extent. Some patients have a very thin outer bone layer, corticalis, which is hard, but the rest of the bone, the inner spongious bone, is very soft. For some patients, on the other hand, all the bone through the entire section is hard.

Self-tapping fixtures have previously been used primarily for softer bone-types, i.e. bone in the over-denture. Self-tapping fixtures for harder bone types must have very good cutting characteristics in order to limit the torsional force so that the fixture itself or the surrounding bone tissue will not be damaged. Very hard requirements on the fixture design as well as on the cutting sharpness then must be fulfilled.

In another, more simple method for using a self-tapping fixture the hole in the jaw bone is drilled big enough to allow only the outer part of the threading to contact the bone. However, this is a risky method as the initial stability of the fixture in the bone is reduced.

SUMMARY OF THE INVENTION

The object of the present invention is to provide a self-tapping anchoring member (fixture) with good properties even when installed in hard bone qualities. According to the present invention the good properties have been achieved by providing the anchoring member with a clearance behind the cutting edges, that is the outer surface of the anchoring member, as seen in a section through the cutting part of the anchoring member, is slightly bevelled behind each cutting edge. By means of such clearance surface the squeezing effect on the anchoring member in the cutting zone when screwed into the bone can be eliminated. This squeezing effect otherwise contributes to a large extent to the torque transmitted to the anchoring member when installed in the bone.

In a preferred embodiment of the invention the clearance is made as a plane surface but it can also be curved.

In the following description the invention will be described in more detail in connection with the accompanying drawing, in which:

FIG. 1 is a side view of the threaded part of the anchoring member according to the present invention and FIG. 2 is a section through the cuting part of the anchoring member.

DETAILED DESCRIPTION OF THE PRESENT INVENTION

Figure 1:
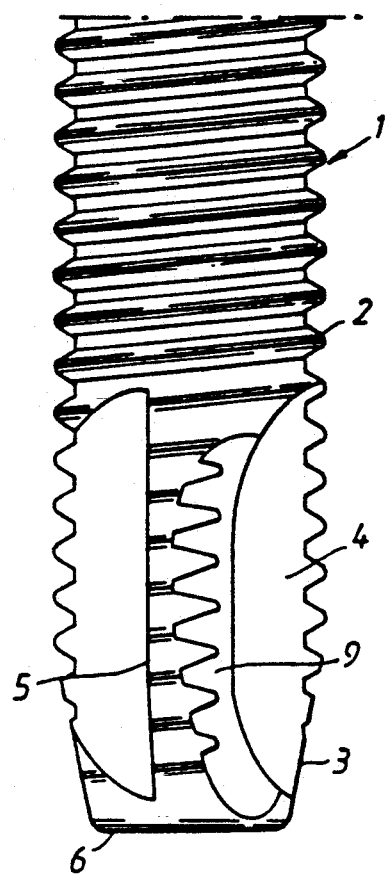

As illustrated in FIG. 1 the anchoring member comprises a cylindrical screw 1 (fixture) with an external thread 2. The screw is intended to be inserted in a bored hole in the jaw bone for permanent anchoring of artificial teeth and tooth-bridges. The neck portion of the screw is therefore intended to be attached to a spacer element, coupling element or the like. These elements take no part of this invention, however, and are therefore not described in any detail here. The anchoring member is preferably made of commercially pure titanium with a surface structure according to SE-PS 7902035-0.

The screw has a conical, downwardly tapered part 3 to facilitate the insertion of the screw into the bored hole in the bone tissue. The cone angle at the tip of the fixture is a parameter which effects the cutting properties. A small cone angle at the tip of the fixture has a positive effect with respect to the guiding and engagement of the screw thread into the threaded bore hole, but it has also a negative effect as an essential part of the important load carrying threaded surface then is removed. In the present embodiment the cone angle is in the range of 15°–40°.

The base of the screw is provided with three openings 4 on the cylindrical surface of the screw. The edges 5 of the openings on the cylindrical surface form sharp cutting edges and the total volume of the openings is big enough to accommodate the scraped-off bone tissue material.

The openings 4 are longitudinal and are extend in the longitudinal direction of the screw close to the end surface 6 of the screw. In this way all scraped-off bone tissue material is collected within the cavities and is stored there and the fixture has a planar, unbroken circular bottom surface 6 without any openings. As illustrated in EP 0 237 505 this is an advantage as the collected bone tissue material promotes newly formed bone tissue to grow into the holes and further prevents any tendencies of screwing out the screw after insertion.

The cutting which is 5 comprises a long, straight edge parallel to the longitudinal axis of the screw. In order to obtain a stable insertion of the screw at least three cutting edges are required, which edges are symmetrically arranged about the periphery of the cylindrical surface of the screw.

Figure 2:
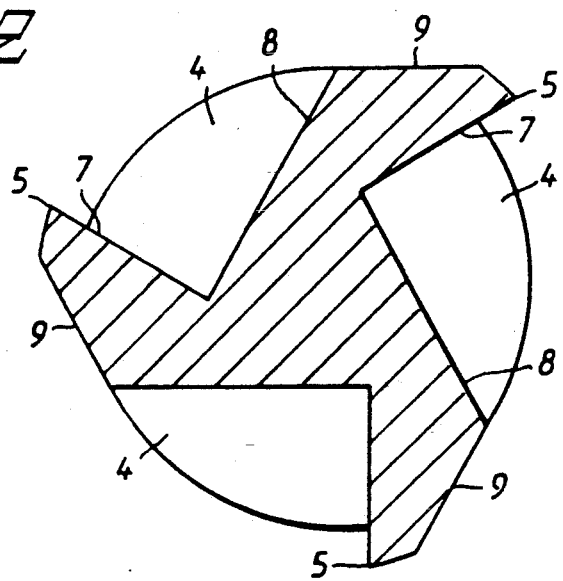

FIG. 2 is a sectional view of the screw which shows the form of the three cavities 4. Each cavity 4 is formed by two perpendicular surfaces, a straight, plane surface 7 with a cutting edge 5 and a concave surface 8, seen in FIG. 1. As in EP 0 237 505 the cavities are formed so as to provide a positive cutting edge. In order to reduce the cutting forces when installing the fixture, it is important that the cutting angle of the fixture is as large as possible. In contrast to the previously known fixture the present invention fixture has an additional clearance 9 behind the cutting edge, that is the outer surface behind the cutting edge 5 is slightly bevelled. This means that the distance from the center of the implant screw to the periphery of the screw in the cutting zone has its maximum through the cutting edge part 5.

This means also that any squeezing effect which might occur when the fixture is screwed into the bone hole can be avoided. Such a squeezing effect could otherwise be an essential contribution to the torsional moment required for installing the screw.

The additional clearance 9 might have different geometrical designs. It might consist of a straight as well as a curved surface. In the example illustrated in the figures the clearance consists of a straight surface located a short distance behind the cutting edge 5 and extend to the concave surface 8 in the cavity.

The cutting process can be divided into two stages, the starting process when the fixture is engaged and the rest of the process when the fixture is screwed down into the bone. By means of the clearance 9 and the positive cutting angles on the cutting edge sufficient starting and cutting characteristics for the fixture even for comparatively hard bone qualities can be achieved.

The prevent invention is not limited to the illustrated embodiment but can be varied within the scope of the accompanying claims.

We claim:

1. A screw-shaped titanium anchoring member having a forward lip for permanent anchorage in bone tissue, specifically permanent anchorage of artificial teeth or tooth bridges in the jaw-bone, comprising at least one cavity located on the forward tip of the screw-shaped member, the edges of said at least one cavity on an outer threaded cylindrical surface forming a cutting portion having a cutting tooth with a cutting edge to provide self-tapping when the anchoring member is screwed into a bored hole in the bone tissue and the total volume of said at least one cavity being adapted to contain scraped-off bone tissue material wherein said cutting edge is provided with a clearance surface defined on the outer surface of the anchoring member, which when seen in a cross-section through a cutting part of the anchoring member, is slightly bevelled a short distance behind said threaded cutting edge.

2. Anchoring member according to claim 1 wherein the clearance surface is a planar surface.

3. Anchoring member according to claim 1 wherein said tip is a conical tip having a cone angle of 15°-40°, and wherein said at least one cavity as well as said clearance surface extend down into said conical tip.

4. Anchoring member according to claim 3 wherein an upper threaded portion of the member forms a non-cutting portion and the thread diameter of the non-cutting portion of the member is less than the thread diameter of the cutting portion of the member.

5. Anchoring member according to claim 1 wherein three cutting edges and three clearance surfaces are symmetrically distributed about the periphery of the outer cylindrical surface of the anchoring member.

6. A screw-shaped titanium anchoring member for permanent anchorage in bone tissue, comprising:
a plurality of cavities located at the forward tip of the member, the edge of each cavity on an outer threaded cylindrical surface of the anchoring member forming a cutting tooth with a cutting edge to provide self-tapping when the anchoring member is screwed into a bored hole in the bone tissue, the total volume of tissue material, wherein the anchoring member on the outer threaded cylindrical surface, a short distance behind each said cutting edge of each said cutting tooth is provided with a clearance surface which, when seen in a cross-section through a cutting part of the anchoring member, is slightly bevelled a short distance behind its respective threaded cutting edge and whereby a distance from the center to the periphery of the anchoring member is larger at each cutting edge than at each clearance surface.

* * * * *